United States Patent [19]
Kowanko

[11] Patent Number: 6,162,395
[45] Date of Patent: Dec. 19, 2000

[54] STERILIZATION OF ELONGATE LUMENS

[75] Inventor: Nicholas Kowanko, Punta Gorda, Fla.

[73] Assignee: Enviromedical Systems, Inc., Minneapolis, Minn.

[21] Appl. No.: 09/135,146

[22] Filed: Aug. 17, 1998

[51] Int. Cl.[7] .................................................. A61L 2/00
[52] U.S. Cl. ............................ 422/33; 422/28; 422/40; 422/292; 422/294; 422/295; 422/297; 422/300
[58] Field of Search ................................. 422/33, 28, 40, 422/292, 294, 295, 297, 300

[56] References Cited

U.S. PATENT DOCUMENTS

| | | | |
|---|---|---|---|
| 5,443,801 | 8/1995 | Langford | 422/294 |
| 5,534,221 | 7/1996 | Hillebrenner et al. | 422/23 |
| 5,711,921 | 1/1998 | Langford | 422/292 |
| 5,753,195 | 5/1998 | Langford et al. | 422/292 |
| 5,759,490 | 6/1998 | Malchesky | 422/28 |

*Primary Examiner*—Krisanne Thornton
*Attorney, Agent, or Firm*—Nikolai, Mersereau & Dietz, P.A.

[57] ABSTRACT

A method of and system for sterilizing the internal surfaces of one or more elongate relatively narrow passages of interest contained in a device of interest, said passages having end openings and being susceptible of sustaining flow therealong by inducing a positive flow of sterilizing gas through each passage of interest in a selected direction. Gas flow through a device of interest is caused by a passive two-chamber device which generates a transient pressure gradient between the ends of the lumens of the device in response to externally imposed variations of pressure. Sterilant gas is provided from outside the two chamber systems.

35 Claims, 6 Drawing Sheets

STERILIZATION OF ELONGATE LUMENS

BACKGROUND OF THE INVENTION

I. Field of the Invention

The present invention relates generally to gas phase (vapor) sterilization and, more particularly, to disinfecting and sterilizing devices having elongate, narrow passages or lumens accessible from both ends such as those commonly associated with vascular catheters endoscopes and similar devices. While the entire device must be sterilized, the invention is primarily concerned with the successful sterilization of the more difficult internal surfaces concurrently with sterilization of the exterior. The invention employs techniques that produce a flow of sterilizing gas through the internal passage or passages in a given load (items to be concurrently sterilized) during processing which results in a rapid and complete exposure of internal passage or channel surfaces of each item of the load to the sterilant vapor by transforming each lumen or other channel or passage of interest into a flow channel for the sterilant gas during successive evacuation and pressurization cycles.

II. Related Art

The need to sterilize articles such as medical devices and instruments following manufacture and initial packaging for use or prior to reuse after contacting a patient has long been recognized. Traditional methods of sterilization include immersion of the article or instrument of interest in a sterilizing solution or the use of various techniques involving elevated temperatures. More recently, however, it has been recognized that chemical vapor sterilization at lower temperatures is generally better suited to today's more sensitive and sophisticated instrumentation and materials of construction. Moreover, financial constraints placed generally on medical care providers presently produce situations in which "single-use" items previously discarded after the first patient are now being resterilized and reused.

While vapor sterilization has offered several distinct advantages over other forms, one major disadvantage heretofore associated with the technique involves an inability to conduct sufficient sterilizing vapor to contact the central internal surfaces of rather long and narrow passages such as the lumens of catheters and endoscopes in an expeditious manner. Typically, present systems operate by partially evacuating the sterilization chamber prior to the introduction of the sterilizing material in a repressurization step. The chamber may be subjected to a series of evacuation pressurization cycles in this manner. Complete sterilization of the internal surfaces depends on diffusion of the sterilant gas, which might be ethylene oxide or another material usually diluted in a carrier gas along the passages from the open ends to produce sufficient antimicrobial activity at the midpoint of each narrow passage. Unfortunately, normal diffusion and other mixing techniques are simply too slow to accomplish reliable sterilization at passage midpoints within desired time constraints and this may offset other advantages of vapor sterilization. The problem is documented, for example, in Alfa, M. J., "Changes In Hospital Practice", *Biomedical Instrumentation and Technology* (September/October 1996) and Alfa, M. J. et al, "Comparison of Ion Plasma, Vaporized Hydrogen Peroxide, and 100% Ethylene Oxide Gas Sterilizer", *Infection Control And Hospital Epidemiology* (February 1996).

Several ways of overcoming the above disadvantage have been proposed with respect to vapor sterilization of relatively long and narrow passages. In one technique, a closed vessel containing a small amount of a vaporizable antimicrobial fluid is attached to one end of an endoscope or other device lumen. A seal is breached in the vessel and the other end of the lumen is exposed to a reduced pressure. This allows antimicrobial vapor to flow along the length of a lumen from the source toward the open end. Such a technique is shown in U.S. Pat. Nos. 5,580,530 and 5,733,503 to Kowatsch et al and in Jacobs et al (U.S. Pat. No. 4,943,414). Another technique shown in Childers et al (U.S. Pat. No. 5,527,508) discloses a pressure modulation technique using a low vapor pressure chemical vapor sterilant in conjunction with a compression carrier gas to promote diffusion in a pressure modulation cyclic sequence. Meanwhile, manufacturers of these devices have been resorting to drastically extended gas sterilization cycles, sometimes taking days to complete, to insure sterility of their device products.

While these previous techniques have met with some success, there remains a need for a method and system that provides more certain and immediate contact between the sterilizing vapor and the internal passage surfaces, particularly the surfaces nearest the midpoint of the passages, to enable the surfaces to be sterilized in an expeditious manner which need not depend on internal diffusive mixing equilibrium.

With regard to certain terminology used in this specification, definitions seem appropriate. The terms "sterilant gas or sterilant vapor" or "sterilizing gas or sterilizing vapor", as used in this specification, refer to any substance, whether true gas or vapor of a volatile liquid, which is capable of sterilizing the load of interest and which is in the gaseous state under use conditions. It may consist of a single active ingredient or a mixture of ingredients, and may contain inactive diluents or carriers. Also, the term "lumen", "channel", "passage", or the like, refers to any internal passage accessible from both ends which is relatively long in relation to its diameter and therefore difficult to readily sterilize near or at its midpoint by diffusion of a sterilant gas from the ends. "Cassette" refers to any relatively compact package form suitable for containing and adapted to receive any of the class of devices (having integral elongate passages) suitable for sterilization and/or storage in accordance with the invention. The cassettes may be of any convenient shape and are assumed to be of sufficient rigidity to withstand the necessary pressure differential used in the method of the invention and the term includes, without limitation, the common rectangular shaped containers. The term "sterilization" means a sufficient reduction in the live microbe and/or spore population to render the device of interest to be safe for its intended use. This is normally a 7–9 $\log_{10}$ reduction of the bacteria and/or spore population.

Accordingly, a primary object of the present invention is to provide an improved method of vapor sterilization particularly suited to the sterilization of devices of interest having internal surfaces including relatively long, narrow passages characteristic of the lumens of catheters and endoscopic instruments, together with devices for carrying out the method.

Another object of the present invention is to provide an improved method of vapor sterilization that is based on inducing a reversible positive flow of sterilant vapor throughout the length of a passage of interest to be sterilized.

Yet another object of the present invention is to establish a positive flow of sterilant vapor throughout the length of a passage to be sterilized by inducing an end-to-end pressure differential to an open-ended passage to be sterilized by exposing each end to a different time variable (transient) pressure function to transform the passage into a flow channel and to promote flow therethrough to produce immediate antimicrobial activity along the entire length of the passage.

Still another object of the present invention is to accomplish the method of the invention using only a passive partitioned cassette to contain the device of interest and a vacuum/pressurization chamber to contain the cassette.

Yet still another object of the present invention is to provide a close tolerance passage or gas permeable collar at the partition wall within the cassette so as to achieve sterilization of the area of the device contacting the partition.

A further object of the present invention is to produce a time variable (transient) end-to-end pressure differential in each open-ended passage to be sterilized on a reversing basis.

A still further object of the present invention is to provide a partitioned two-chamber cassette to contain a device having an elongate passage to be sterilized with one end in each chamber having gas permeable accesses in each chamber to be exposed simultaneously to vacuum/pressurization sterilization cycling in which the combination of the relative chamber sizes and permeabilities can be used to determine the time variable pressure difference between the chambers.

These and other objects, as well as these and other features and advantages of the invention, will become apparent to those skilled in the art upon familiarization with the specification, drawings and claims contained herein which are meant to exemplify but not to limit the scope of the present invention in any manner.

SUMMARY OF THE INVENTION

The present invention provides a new method and apparatus for achieving timely total gas or vapor sterilization in devices generally having internal passages which are difficult to sterilize utilizing diffusion techniques. These include, for example, the elongated lumens of vascular catheters and the interior passages of endoscopes. The present invention achieves rapid vapor sterilization by providing for immediate and complete contact between the internal surfaces of the instrument passages and the sterilizing vapor by providing means which produce a flow of sterilant gas in and throughout the entire length of the passage of interest to be sterilized. The present invention enables a variety of open-ended passages including the long, narrow tubes or instrument passages of endoscopes or catheter lumens to be dependably sterilized internally in a timely manner even at the most difficult central portion of the load. The method adapts to a number of apparatus embodiments, some of which are illustrated in the detailed description by way of example, and lends itself to the use of existing equipment.

The present invention introduces a method and apparatus for gas phase sterilization of elongated tubular devices of interest in which sterilant gas flow through lumens of the devices of interest is induced by a flow-dependent transient pressure gradient set up between the ends of the lumens. The transient pressure gradient can be created by exposing each end of each lumen to a separate chamber and concurrently evacuating or concurrently pressurizing both chambers at different effective rates. A preferred method is one in which each end of a passage of interest in a device to be sterilized is subjected to a different transitory pressure change function when a sterilization container containing the device is exposed to a vacuum or pressurization step thereby producing a transitory pressure gradient function between passage ends which transforms the passage of interest into a flow channel and induces a flow of sterilant gas along the length of the passage. The different transitory pressure change functions may be produced in any of a number of ways which result in the net effect of a pressure gradient which typically operates to induce a flow of sterilant material in one direction when the ambient pressure is reduced as by a vacuum pump or in the opposite direction when the pressure is increased by the introduction of sterilant gas.

A device to be sterilized is generally loaded into a storage container, preferably in the form of a cassette, which may be of a design unique to that species of device. The container is provided with two compartments or chambers of equal or unequal, but relatively fixed size. At least one of the chambers has an area of vapor permeability that access the volume outside the cassette. When a device is loaded for sterilization, one end of each of the elongate passages or lumens of interest is situated in each chamber. By modulating the pressure outside the cassette, both chambers are subjected to evacuation/pressurization cycles with sterilant gas being added in the pressurization cycles in a manner that effectively affects the chambers according to different transitory pressure change functions and thereby induces a flow between the chambers in the passages of interest. Flow in one direction during evacuation reverses during pressurization.

The chamber sizes and difference in the transitory pressure change functions are preferably sufficient to cause at least one complete volume change in all passages of interest. It will be appreciated that a net flow that amounts to less than one volume change will also eventually result in sterilization in accordance with the invention; however, additional cycles and thus a longer sterilization time will be required with lesser flow amounts. As used herein, net flow means the flow through the passages of interest during one pressurization or evacuation cycle. Flow through the passage of interest can be accomplished in a number of ways. If the two cassette compartments are unequal in size, evacuating or pressurizing them at the same volumetric rate will produce a different rate of pressure change in the compartments to produce the desired effect. Of course, to produce a volume change, the smaller volume chamber must still have a volume that exceeds the total volume of the passages to be sterilized. If the cassette compartments are not sufficiently unequal in size, relatively diverse volumetric flow rates for evacuation/pressurization can be used to compensate. Relative flow rates can be adjusted in a number of ways according to the invention. For example, the two chambers of the cassette may be provided with gas permeable accesses of different capacities and the cassette exposed to the cycle steps within a common larger sterilizing chamber or the chambers may be connected to vacuum/pressurization devices that effectively treat them unequally due to size of connection, relative permeability, etc.

Direct cross flow through the barrier between the chambers is minimized by a low clearance fit or by sealing devices between the item to be sterilized and the barrier wall. The seal is preferably a resilient, but porous material such as a foam material that allows seepage but not direct flow. However, a relatively low clearance fit may also be used. It is an important aspect of the invention that the entire device be sterilized and, accordingly, sterilant material must readily reach and sterilize that segment of the device which is in the vicinity of the barrier or partition, either directly or through a porous material. It is noteworthy that the method can manifest itself in any of a variety of devices and technique combinations and offers a new practical solution to a long-standing problem.

In accordance with the operation of the device or method of the invention, when the assembly is evacuated, gas will flow from both chambers, however, since the time related transient flow function for each is different, the pressure within one chamber will drop faster than that within the other chamber. This temporary pressure differential will induce a net flow of gas throughout the length of the tubes or passages to be sterilized inside the cassette. Conversely, upon repressurization with sterilant gas, the net flow will reverse as the same chamber will fill more readily. By cycling the system, this technique produces two-way time varying or transient, reversing flow of relatively full strength sterilant gas to maintain high antimicrobial activity along the entire length of the device to be sterilized. The rate of depletion of sterilant material potency in use should also be considered in arriving at ideal cycle times. The typical pressure range for the operation of the process may cycle from less than 1 Torr to several atmospheres.

The required time and number of cycles also will vary with the type of items to be sterilized and the previous histories of those items. Typically, 2 to 5 evacuation/pressurization steps are required.

Of course, the open-ended internal passages or lumens of interest need not run the length of the device; they only need straddle the barrier between the chambers. Thus, guidewire or other shorter lumens contained some devices in addition to much longer lumens may be sterilized by proper placement of the device so that one access opening is on either side of the barrier.

Any sterilant material compatible with the material of the endoscope or other device being sterilized may be employed as the sterilizing vapor. For example, one may employ ethylene oxide (ETO), hydrogen peroxide ($H_2O_2$), formaldehyde (HCHO) or a variety of peracid materials such as those disclosed in applicant's copending application, Ser. No. 08/032,606, filed Mar. 17, 1993. Purge cycling, as required, is used to remove chemical sterilants after sterilization.

Of course, those skilled in the art will recognize that sterilant material is consumed by impurities during the sterilization process which, in turn, reduces the strength or anti-microbial capacity or potency of the gas unless the sterilant is replenished. This is particularly true in confined spaces. The flow-through system of the invention changes the gas within even the most clandestine central passage spaces often enough to enable the strength of the sterilant to be maintained at a relatively high level throughout the load during the process.

The invention may also operate using a single access. One single access embodiment that employs the technique of the present invention involves providing one end of an open-ended endoscope tube or other elongated open-ended hollow device to be treated with a closed chamber in the form of a removable gastight hollow fitting (cap or bulb) of internal volume greater than the internal volume of the device to be sterilized to assure sufficient flow through during sterilization. The hollow fitting preferably includes a gas permeable collar that fits over the endoscope tube or the end of another device of interest constructed so that the area under the collar is also exposed to the sterilant gas and the entire device is sterilized. This system is designed to be placed in a packaging container that, in turn, is itself placed entirely inside of a pressure variable gas sterilization chamber for processing. In this manner, the packaging container becomes a second chamber which contains the first, i.e., the larger chamber entirely contains the smaller with the passages of interest situated therebetween with respect to flow. A similar effect is realized when one compartment of the cassette embodiment is sealed and the entire system is forced to "breathe" through the other via the passages of interest.

During sterilization, the pressure is cycled on a time variable basis as with the cassette system previously described. The packaging container is first partially evacuated and thereafter the desired amount of active sterilant gas is admitted. Sterilant gas entering the chamber enters each partially evacuated lumen at the exposed open end thereof and flows through each entire device passage to equalize the pressure in the cap, bulb or closed cassette chamber volume thereby providing a fresh stream of sterilizing gas throughout the length of the tube. During subsequent evacuation stages of the sterilizer chamber, the stored excess of vapor within the volume of the cap, bulb or closed cassette chamber will flow out again sweeping through the entire length of the hollow lumen providing further contact with the entire inner surface.

Alternatively, the device may be enclosed in a gas permeable container or bag and the tightly fitting chamber placed over one end of the package so as to enclose one opening of the device lumens, the package or bag acting as a gas permeable collar. This embodiment is especially useful for endoscopes packaged to be stored hanging in a straight posture. It will be appreciated that the cassettes or other such devices of the present invention readily replace typical contemporary flow-through (gas permeable) sterile soft-sided packaging (some of which are also known as peel pouches), and which can be used with some single access versions of the present invention. The cassettes or cap or bulb devices should be rigid enough to resist flexure during cyclic pressure changes although large pressure differentials do not normally occur.

BRIEF DESCRIPTION OF THE DRAWINGS

In the drawings, wherein like numerals are utilized to designate like parts throughout the same.

DETAILED DESCRIPTION

The present invention offers a method for gas phase sterilization of elongated tubular devices of interest, such as medical catheters and endoscopes, in which sterilant gas flow through the lumen(s) of the devices of interest is induced by creating a different transient pressure gradient function at each end of those lumens. The transient pressure gradient is preferably created by exposing each end of each lumen to a separate chamber and concurrently evacuating or concurrently pressurized both chambers at different effective rates. The method can be practiced using any of a variety of sterilization devices and provides new flow-through approaches to the total gas or vapor sterilization of relatively elongate narrow open-ended passages in medical and other devices requiring sterilization that enables rapid and total sterilization by virtue of providing a positive flow of sterilizing gas contacting all internal surfaces. As indicated, the approach is particularly suited to long and narrow passages with end openings, the central portions of which have heretofore challenged and resisted timely vapor sterilization because of the difficulty in accessing these regions with effective antimicrobial concentrations.

It will be appreciated that any suitable sterilant gas may be used in accordance with the present invention including ETO, $H_2O_2$, HCHO, ion plasma sterilizers, peracids, including performic acid, peracetic, perpropionic acid and mixtures thereof as more completely described in the above-cross referenced copending application. The techniques of the invention are particularly useful for cold sterilization which, as used herein, refers to procedures which effect sterilization at temperatures substantially below the 120–132° C. typically employed using high pressure steam techniques.

In addition, any suitable range of pressures may be employed in implementing the techniques of the invention, although a range which centers at or below one atmosphere is generally the easiest to implement. The process is also generally designed to enable operation at relatively low sterilization temperatures, i.e., below 100° C. and preferably below 70° C. In addition, any type of device having intricate internal passages which are openly accessible but difficult to reach by diffusion and which will admit to sterilization using the present invention are presumed to be intended to be included and those illustrated, together with the particular embodiments or devices to carry out the invention, are given by way of example and not limitation.

Figure 1:
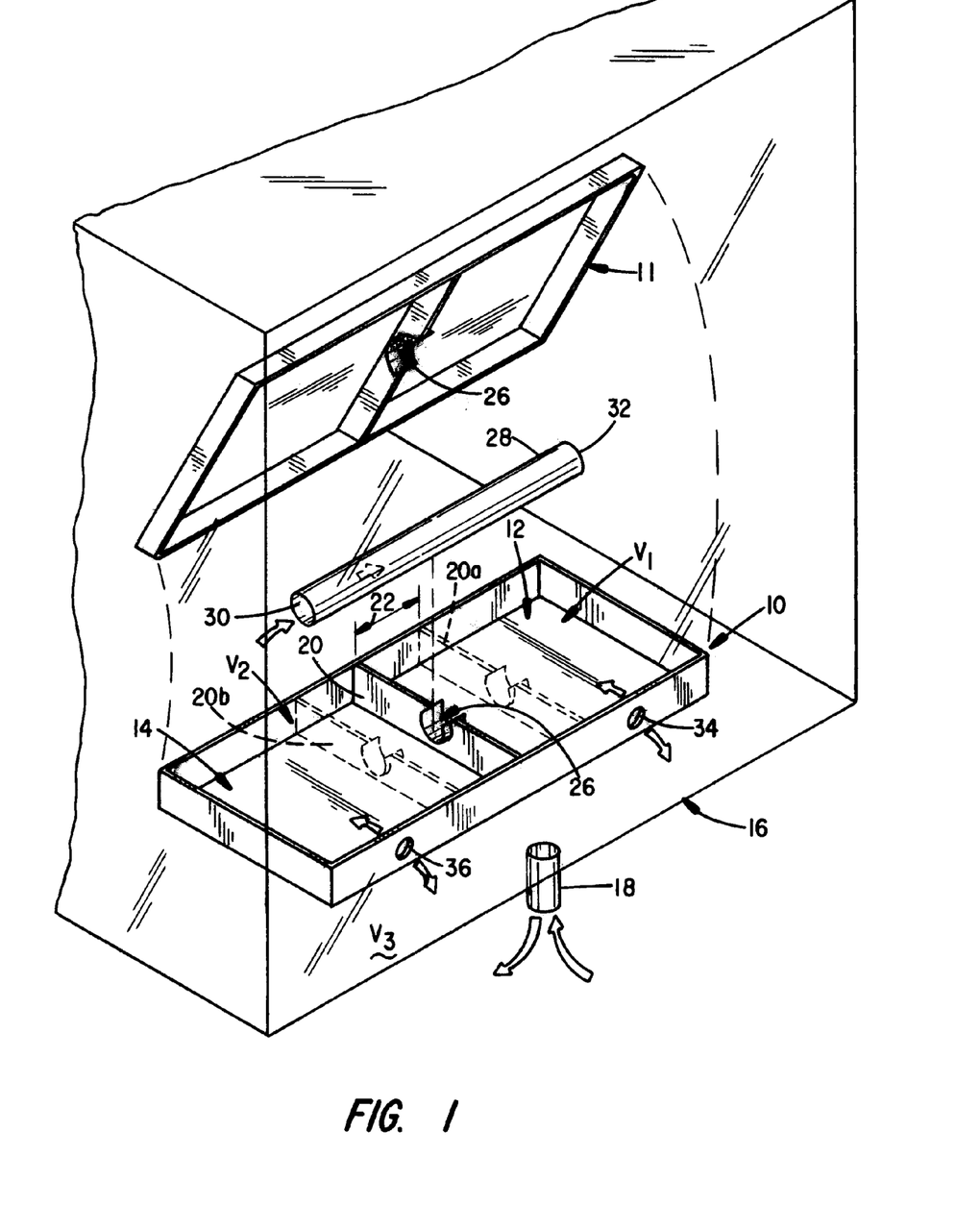
FIG. 1 illustrates schematically a perspective view of a two-compartment cassette system for accomplishing vapor sterilization in accordance with the invention.

FIG. 1 depicts a preferred embodiment in which a hollow sterilizing cassette package or container having a body generally at 10 and a removable lid 11 is nominally subdivided into unequal compartments including a first small chamber or compartment 12 of volume $V_1$ and a second chamber or compartment 14 of volume $V_2$. The cassette package including body 10 and lid 11 is shown inside a larger sterilization chamber shown as a transparent fragment at 16 of volume $V_3$ which is attached by one or more external accesses represented by 18 which represents both a gas admitting or supply system that includes a source of sterilizing and/or purge gas 36 and to a vacuum system (not shown) in a well-known manner. Separation of the compartments 12 and 14 is accomplished by a separator barrier or partition 20. The separator 20 as indicated by the arrow 22 may be located in a variety of locations as shown in phantom at 20a and 20b depending on the desired relative sizes of $V_1$ and $V_2$ and generally contains one passage or opening therethrough, which is illustrated as having components or portions in the body 10 and lid 11 at 26 to accommodate an elongated, hollow tube 28 to be treated. The tube is situated with one open end 30 in the compartment 14 and the other open end 32 in the chamber 12. When the cassette is asesmbled, the passage 26 should be snug with, but not in gastight relation to the tube 28. A snug fit between the tube 28 and the barrier 20 minimizes direct flow between the chambers, but allows leakage for sterilization of the entire device is all that is necessary. External vapor-permeable areas accesses or ports connecting to the container 12 are represented for the chambers 12 and 14 respectively by 34 and 36, and optionally also by 26. The tube 28 represents any elongated device lumen or passage and the areas 34 and 36 represent accesses of any size or degree of permeability. It will be understood that the lid 11 and body 10 are provided with the necessary peripheral seals when assembled.

The embodiment of FIG. 1 is designed to operate by pressure modulation in the chamber 16 ($V_3$) using alternating evacuation and sterilizing gas input or pressurization steps for sterilization as through access 18. Generally, $V_3 >> (V_1 + V_2)$ and a wide range of ratios between $V_1$ and $V_2$ is acceptable when the transport capacity of accesses 34 and 36 are of the same or nearly the same vapor transporting capacity provided that one is larger than the other. The higher the ratio, the greater will be the transient pressure gradient allowing the selection of an optimum ratio for a particular application, pumping rate, etc. However, the smaller chamber should still be greater than the total internal volume of the lumens to be sterilized. Typically, the desired ratio between $V_1$ and $V_2$ is from about 2:1 to about 20:1; however, lower or higher ratios may be employed if desired.

Both compartments 12 and 14 may alternatively be connected via a conduit arrangement attached at 34, 36 (not shown) to a common source of sterilizing vapor and a common evacuating system in a well known manner. In addition, the connecting vapor-permeable accesses may be unequal in vapor transmission capacity to thereby produce a difference in effective rates of pressurization and evacuation for the two chambers. In this variation, the two compartments 12 and 14 may be equal or unequal in volume. Also, only one access need be used in one embodiment where the system interfaces through only one chamber. This represents one version of a single access system and can be accomplished by closing one port or vapor permeable access 34, 36. The vapor passing or transmitting capacity of the areas 34, 36 may be varied by adjusting size, permeability or both and that may be combined with sizing the compartments 12 and 14 to produce any conceivable combination. The rate of change of the external pressure in the main chamber represented by 16 or $V_3$ can also be varied.

Figure 2:
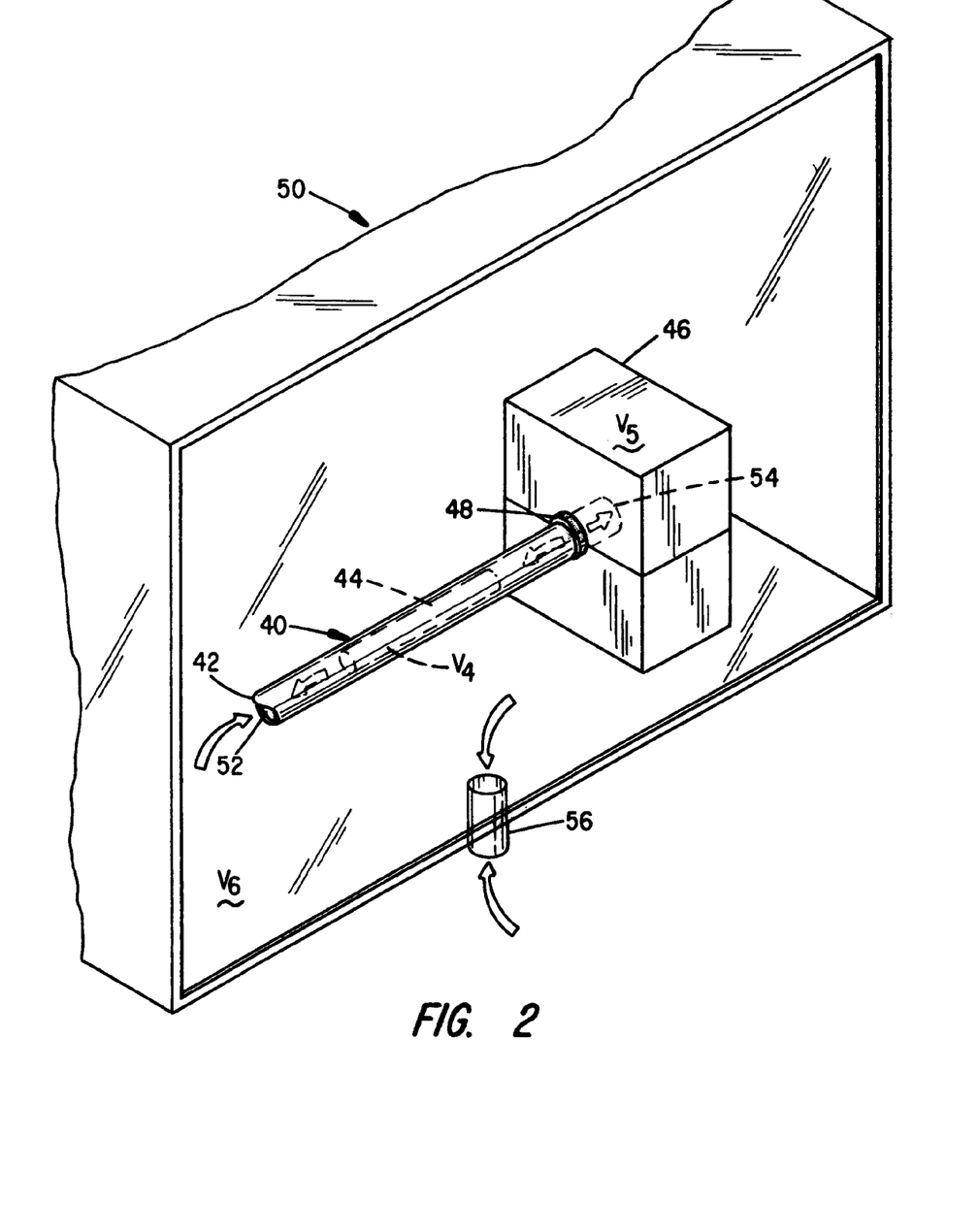
FIG. 2 is a schematic perspective diagram of an enclosed lumen and bulb single access arrangement for a device to be sterilized in accordance with the invention.

FIG. 2 illustrates a single access configuration in which a first chamber $V_5$ is entirely contained within a second $V_6$ and the lumen of interest $V_4$ extends between $V_5$ and $V_6$. It will be recognized that this is similar to removing either $V_1$ or $V_2$ in FIG. 1 and sealing the remaining access to the outside 34 or 36 such that the function of the remaining chamber ($V_1$ or $V_2$) is assumed by $V_3$ which, of course, preserves the general principle of FIG. 1. An elongated tube generally at 40, shown broken at 42, illustrates an elongated internal lumen at 44 which encloses or contains a total volume denoted as $V_4$. A hollow cap or bulb 46, having an internal volume $V_5$, is shown attached to the tube 40 using a gas permeable collar 48. This assures sterilization of the entire device. This system is further enclosed in a chamber or package shown transparent and broken at 50 which has an internal volume represented by $V_6$. Both end accesses 52 and 54 of the tube 10 are open so that a free flow between $V_5$ and ambient through $V_4$ may be established, together with flow penetrating the collar 48. The relative sizes of $V_4$ and $V_5$ are without restriction except that, to promote timely sterilization, $V_5 \geq V_4$. A preferred range of ratios between $V_5$ and $V_4$ is from approximately 1 to 10 with a most preferred range of about 2–4. Of course, normally $V_6 >> V_5 + V_4$. This will depend on the nature of the device to be processed.

In this embodiment, the entire assembly including the attached cap or bulb is designed to be subjected to sterilization in a common package represented by chamber 50, which may be placed in a sterilization chamber as at 16 in FIG. 1. The package 50 is shown having a permeable access 56 and an internal volume $V_6$. Of course, the ratio of $V_5$ to $V_4$ designed for a particular sterilant or sterilization process, such that cycling of the pressure in $V_6$ produces sufficient reversible flow through the opening 52 to enable the entire volume $V_4$ to be purged quickly in both directions by the actual or net flow in and out of $V_5$.

In operation, the sterilization chamber containing the device of FIG. 2, including dimensionally stable flow-through container 50 is, in turn, placed in a conventional sterilization chamber (not shown), made accessible to a vacuum system and a pressurization system through the access represented by 56 which may be similar in configuration to 34, 36 of FIG. 1. The volume $V_6$ is first evacuated to a desired pressure below atmospheric causing outward flow to equalization. Thereafter, sterilant gas with or without a carrier gas, as desired, is introduced into the chamber 50 and, as the pressure in $V_6$ increases, an amount of this flows inward through the opening 52, through lumen 44 and through the opening 54 into $V_5$. This amount exceeds the volume $V_4$ so that complete purging and contact with the entire internal surface of the lumen 44 by the sterilizing gas is assured. These steps are cyclically repeated at desired timed intervals until sterilization is completed. After sterilization, the system may be subjected to one or more cycles using a purge gas such as $N_2$ to remove sterilant material.

Figure 3:
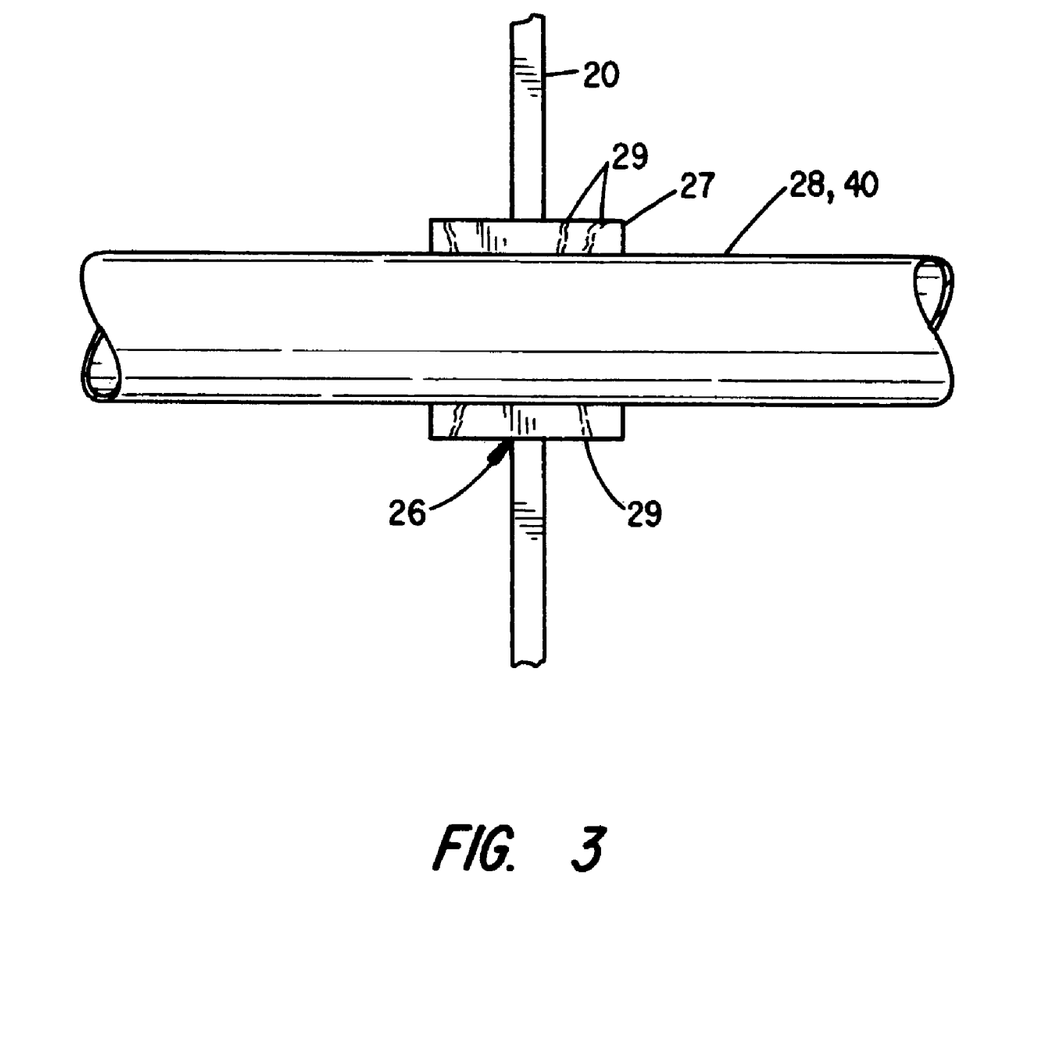
FIG. 3 illustrates in perspective a greatly enlarged interchamber transition area as in FIG. 1 partially cut away to show portions of the interior and a gas-permeable layer.
Figure 4:
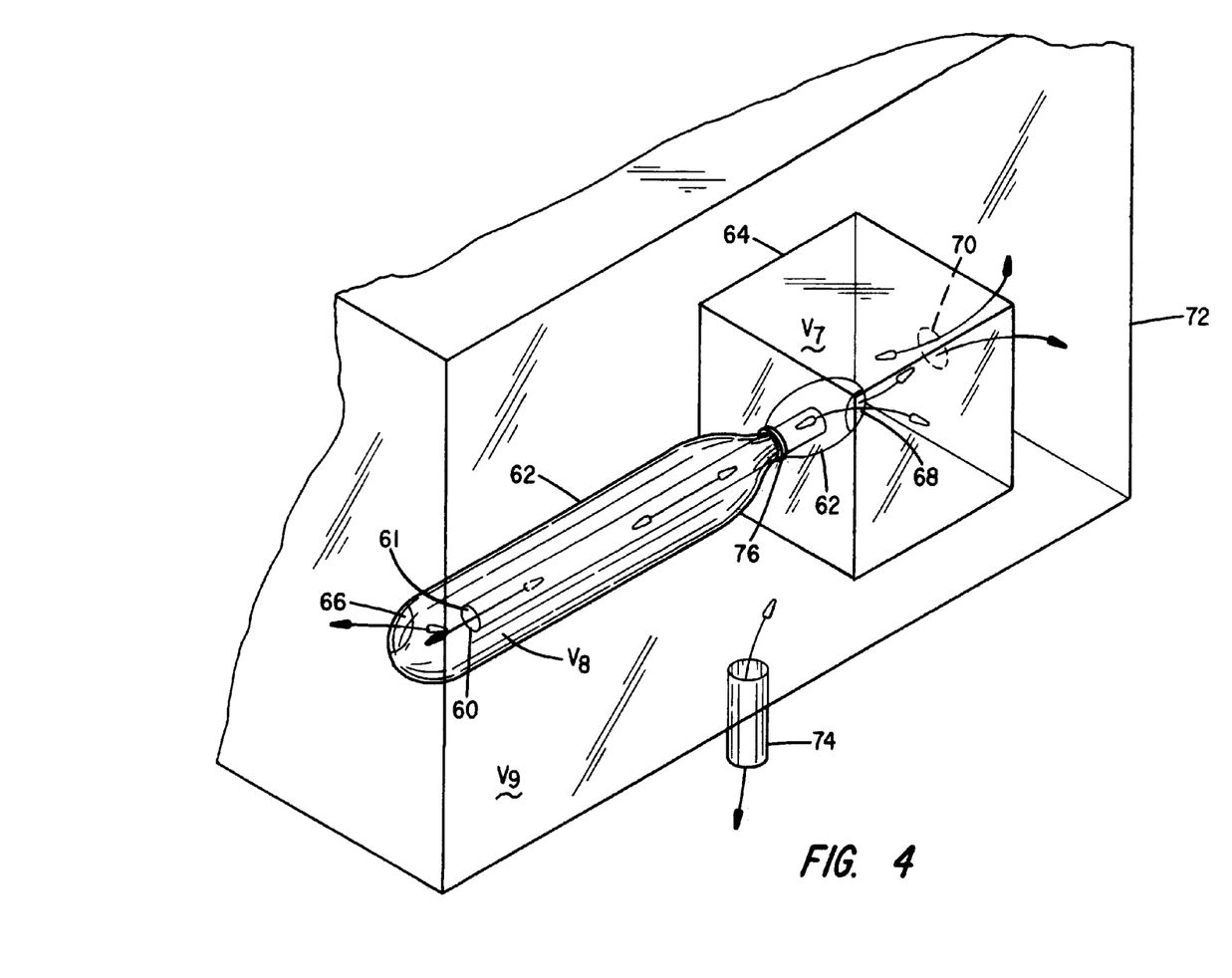
FIGS. 4 and 5 schematically illustrate in perspective a further adaptation or variation useful for processing endoscopes.
Figure 5:
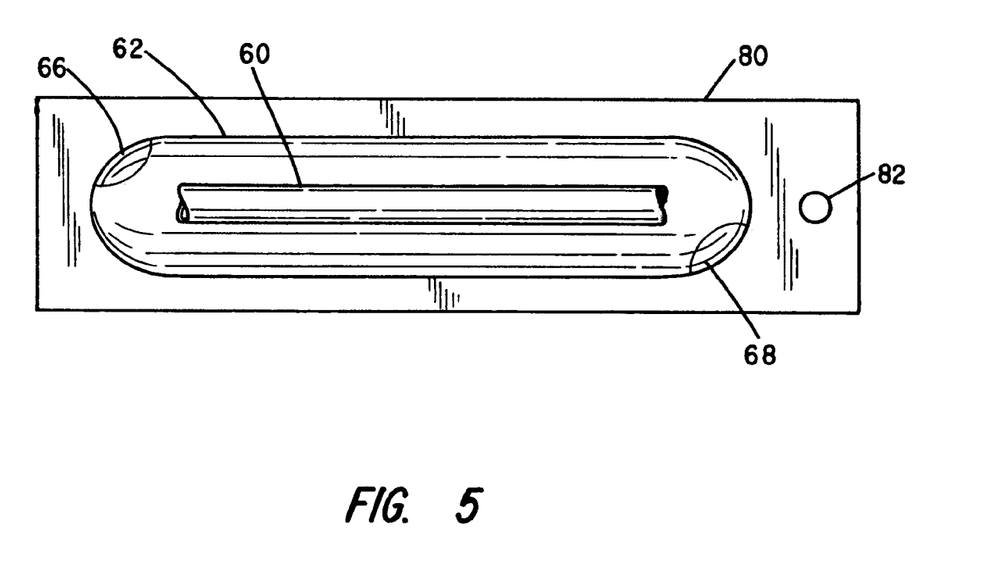

An additional embodiment or configuration is illustrated in FIGS. 4 and 5 in which an endoscope device 60 with open-ended lumen 61 is sterilized in a storage package 62 that later is mounted to enable hanging storage in a straight configuration. In FIG. 4, the package 62 is shown protruding through an opening and partially deployed in a container 64 having a volume $V_7$. Vapor permeable or gas transport areas in the wall of the package 62 are represented by 66 and 68 and an optional permeable area is shown in the otherwise sealed container 64 at 70. The passage of the package 62 into the container 64 may be similar to the interchamber transition area illustrated in FIG. 3. The volume of the package may be represented by $V_8$. The system including the container 64 and package 62 may be placed in a sterilization chamber 72 having a volume $V_9$ and an external connection as at 74 which is conventionally connected to a vacuum line and source of sterilant vapor or purge gas according to known techniques. In FIG. 5, the package 62 is shown mounted on a backing 80 for hanging on a hook as by using opening 82.

It will be apparent from the above discussion that the system of FIG. 4 may be operated according to the method of FIG. 1 when optional transport area 70 is provided and according to the method associated with FIG. 2 without it. While the container 64 is represented as a cubic or box-like structure, it will be appreciated that it can be of any desired shape so long as it functions in the manner intended. This, of course, is also the case with respect to the hollow cap or bulb 46 of FIG. 2 and the cassette and lid combination of FIG. 1. Moreover, the opening in the container 64 may be in the form of a clamping device or any other confining mechanism that fits over one end of the package 62 to cause vapor material flowing between the package 62 and the container 64 to predominantly use the lumen 61. Thus, for example, the chamber or container 64 may be a clamp-on envelope device.

Figure 6:
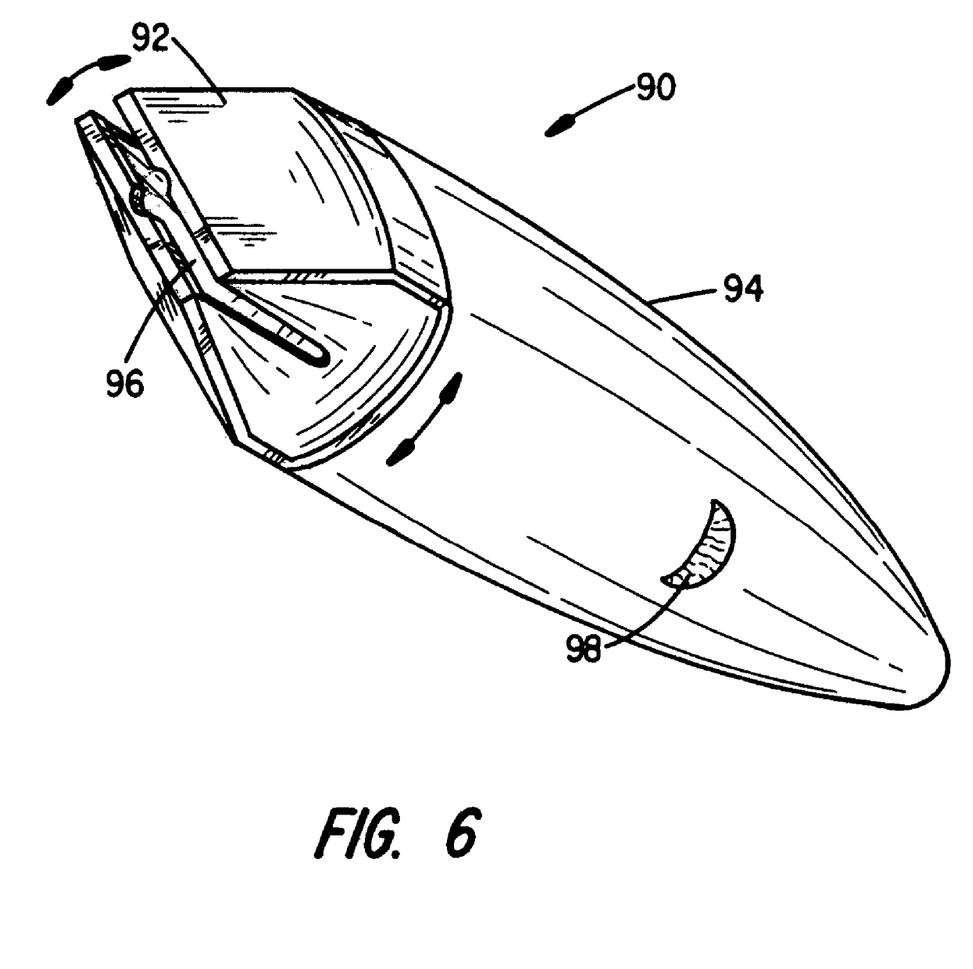
FIG. 6 depicts in perspective an alternate embodiment of the cap or bulb of FIG. 2 or the container of FIG. 4 for receiving one end of a device to be sterilized.

Such an alternate container is shown at 90 in FIG. 6 which includes a spring clamp 92 connected to a semi-rigid structure 94. The clamp 92 provides an opening 96 adapted to receive a tube as at 40 in FIG. 2 or a package as at 62 in FIG. 4 and may have a vapor transport permeable as at 98. The clamp 92 is operable to engage a tube or package for sterilization as needed.

In operation, the sterilization cycle for the embodiment illustrated in FIG. 1 begins with the evacuation of both chambers 12 and 14. If the chambers are unequal in size, because of the difference in volume between the two chambers, the pressure in the smaller chamber volume initially decreases more rapidly than that of the larger one thereby producing a transient pressure gradient between the two chambers. This imbalance induces a net flow through the tube 28 from the larger chamber into the smaller chamber which continues until the pressure finally equalizes at the end of the evacuation portion of the sterilization cycle. In the next step, sterilant vapor is introduced into both chambers and a reverse imbalance occurs with the pressure rising faster in the smaller compartment than in the larger compartment thereby inducing a gradient which results in a flow through the tube 28 and collar 26 from the smaller chamber into the larger chamber until pressure equalization is again reached. Sterilization is accomplished by a series of cyclical alternate pressurization and evacuation steps, each resulting in a purging and replacement of the gas atmosphere within the tube 28, thereby assuring complete sterilization of the inner surfaces of the tube. Of course, a similar effect can be produced by varying the vapor transport capacity of the ports 34, 36 accessing compartments. A higher capacity for vapor transmission produces the effect of making the chamber smaller. As above, a number of purge cycles may be used at the end of the process to remove traces of sterilant material from the cassette.

While the figures illustrate several embodiments, it should be kept in mind that many other possible configurations can be used which will enable the practice of the present invention. Thus, cassette 10 or package 62 may replace peel pouch package for containing an endoscope, medical catheter or the like. In addition, the system can be configured to operate with separate vacuum pumps and pressurization devices attached at 34, 36 so long as these are properly controlled and coordinated in order to achieve a desired transient or time variable pressure gradient between the ends of the internal lumens of the device to be sterilized. These accommodations are considered well within the general knowledge of those skilled in the art.

As indicated above, an important aspect of the invention is the total sterilization of the device of interest and, in this regard, the passages or openings between the chambers as at 26 in FIG. 1, 48 in FIG. 2 and 76 in FIG. 4 are provided with gas or vapor permeable material at the interface with the device so that these areas remain exposed to the sterilant gas during the process. Thus, the passages 26 and 48 may be appropriately aligned as at 27 in FIG. 3 of the material that prevents direct cross flow between the chambers but one which is highly porous to allow penetration of the sterilant vapor through the layer 27 to the surface of the device as at 28. A few porous openings are illustrated in FIG. 3 at 29, but it will be appreciated that the entire surface of the device 28 will be adequately exposed to sterilant gas during the process. Alternatively, a low clearance fit of low leakage may also suffice.

While the above description has emphasized elongated devices having a single open-ended lumen, multiple lumen devices such as vascular catheters having a plurality of parallel lumens or multi-lumen scoping devices can also be processed as a number of parallel elongate passages can be sterilized readily as well utilizing the techniques of the present invention. The relative volume relationships, of course, need reflect the total volume of the devices of interest. Additionally, it will be understood that a sterilization chamber may be used to simultaneously (concurrently) process a plurality of the illustrated or other devices in accordance with the invention. For example, the barrier 20 may be provided with a plurality of openings 39 to accommodate a plurality of tubular devices 26 or a plurality of cassettes or devices 10 can be provided in a batch to be sterilized in a common chamber.

This invention has been described herein in considerable detail in order to comply with the patent statutes and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method of gas phase sterilization of devices of interest of a class having internal surfaces which include one or more elongate passages of interest, said passages having end openings and being susceptible of sustaining a flow of gas therealong the method comprising the steps of:
   (a) connecting an empty removable closed chamber to said devices of interest to one end of said passages of interest, said closed chamber being open to each said passage of interest and wherein said closed chamber has a volume greater than the total volume of all connected passages of interest to be sterilized;
   (b) establishing a net flow of sterilant gas through each passage of interest in a selected direction by subjecting the one or more end openings not connected to said removable closed chambers to transient alternating cycles of decreasing pressure and pressurization thereby producing a directionally reversing net flow through said one or more passages of interest;
   (c) introducing sterilant vapor with said repressurization steps of said cycles; and
   (d) varying said pressure sufficiently that said net flow in each direction exceeds the volume of said one or more passages;
   (e) providing vapor permeability for sterilizing the portion of said devices of interest at the connection with said closed chamber.

2. The method of claim 1, further comprising the step of:
   (f) enclosing said device of interest with said removable closed chamber attached in a storage container having a gas permeable, external access port for evacuation and pressurization.

3. The method of claim 2 further comprising the step of:
   (g) enclosing said storage container in a larger sterilization vessel for pressure cycling.

4. The method of claim 1 wherein said device of interest contains a single passage of interest.

5. The method of claim 1 wherein said device of interest contains a plurality of passages of interest.

6. A gas sterilization system to sterilize devices of a class having an elongate, narrow-internal passage of interest, said system comprising:
   (a) a first sterilization chamber having an internal volume and an opening for receiving an end portion of a storage package containing a device to be sterilized, said end portion further containing one end of said passage of interest and a vapor permeable gas transport area;
   (b) a storage package for containing the device of interest in a generally straight configuration and containing a plurality of vapor permeable gas transport areas;
   (c) a second sterilization chamber for containing said first chamber and said package, one end of said package being received in said first sterilization chamber;
   (d) said second sterilization chamber having a connection device to connect to an evacuation system disposed to draw a vacuum in said second chamber to thereby reduce the pressure in said package and said first sterilization chamber at an unequal rate and a pressurized sterilant gas introducing system disposed to introduce sterilant gas into both of said chambers at an unequal rate.

7. The gas sterilization system of claim 6 wherein said first sterilization chamber further comprises a vapor permeable area open to said second sterilization chamber.

8. The gas sterilization system of claim 6 wherein said first chamber clamps on to said storage package.

9. The gas sterilization system of claim 7 wherein said first chamber clamps on to said storage package.

10. A method of gas phase sterilization for devices of interest of a class having internal surfaces which include one or more elongate passages of interest, said passages of interest having end openings and being susceptible of sustaining a flow of gas therealong, the method comprising the steps of:
    (a) providing an ambient atmosphere containing sterilant vapor;
    (b) exposing both said end openings of each passage simultaneously to an increasing or decreasing pressure wherein each end of a given passage is exposed to a different transitory pressure function to thereby establish a net flow of sterilant gas through each passage of interest in a selected direction; and
    (c) alternately and simultaneously cyclically exposing said end openings to decreasing and increasing pressure change thereby alternately reversing the direction of net flow of sterilant gas through each passage of interest, wherein the volume of said net flow induced through each passage of interest in each direction during each cycle is greater than the volume of that passage of interest.

11. The method of claim 10 wherein the device of interest contains a plurality of passages of interest.

12. A method of gas phase sterilization for devices of interest of a class having characteristic internal surfaces which include one or more elongate passages of interest, said passages of interest having end openings and being susceptible of sustaining a flow of gas therealong, the method comprising the steps of:
    (a) enclosing said device of interest in a package having two chambers, a common partition member forming said chambers in said package, said device breaching said partition member such that each end opening of each said passage of interest lies in a different one of said two chambers and wherein at least one of said two chambers has an externally communicating gas transport capability area;
    (b) placing said package in a larger sterilization chamber;
    (c) providing an ambient atmosphere containing sterilant vapor;
    (d) exposing said package to an increasing or decreasing ambient pressure, the package being constructed so that each end of a given passage is thereby exposed to a different transitory pressure function to thereby establish a net flow of sterilant gas through each passage of interest in a selected direction;
    (e) subjecting said package to cycling pressurization and vacuum steps using pressure modulated sterilant gas thereby alternately reversing the direction of net flow of sterilant gas through each passage of interest; and (f) wherein the relative volumes of the two chambers of the package in combination with the relative externally communicating vapor transport capabilities of the two chambers are designed in combination to produce a desired net flow volume of sterilant gas greater than the volume of the passages of interest to be sterilized at a given pressurization and vacuum cycle modulation.

13. The method of claim 12 wherein both of the compartments have an externally communicating gas permeable area.

14. The method of claim 12 wherein one of said compartments is larger than the other.

15. The method of claim 12 wherein said device of interest breaches said common partition between said two chambers through an opening that is surrounded by a vapor transporting gas permeable medium such that areas of the device in the vicinity of the partition are sterilized.

16. The method of claim 12 wherein said device of interest passes between said two chambers through an opening in said common partition in a manner and such that sterilant material may pass between said partition and said device.

17. The method of claim 12 wherein only one of the chambers has an externally communicating gas permeable area.

18. The method of claim 12 wherein the effective rate of evacuating or pressurizing each of said separate chambers is accomplished at least in part by providing externally connecting gas permeable areas in said chambers having different vapor transport capacities.

19. The method of claim 12 wherein the relative volumes of the chambers and the relative vapor transport capabilities of the gas permeable areas in combination are sufficient to produce a net flow volume of sterilant gas greater than the volume of the passages of interest to be sterilized.

20. The method of claim 12 wherein said chambers are of unequal volume and the size and size ratio of the volumes of said sterilization chambers are sufficient to produce a net flow volume of sterilant gas greater than the volume of the passages of interest to be sterilized.

21. A sterilization container for containing a device of interest to be sterilized of a class having internal surfaces which include an elongate passage of interest comprising:
(a) a shaped cassette module intended for a particular device of interest including a hollow body and a lid and enclosing a volume;
(b) a partition in said sterilization cassette to divide said volume into two compartments, said partition further being provided with one or more partition openings therein to accommodate the nesting of a portion of a device of interest to be sterilized extending therethrough such that each internal passage of interest to be sterilized in said device can be disposed to have a passage opening exposed in each of said compartments;
(c) said cassette being provided with a gas permeable vapor transport area open to the exterior in at least one of the two compartments; and
(d) wherein said cassette is adapted to be contained in a larger sterilizing vessel during the sterilization operation.

22. The container of claim 21 wherein the combination of relative sizes of said two compartments and vapor transport capacities of said one or more gas permeable accesses to external ambient are such that exposure of the entire cassette to an environment of desired reduced pressure will result in a desired amount of net transient flow induced along the length of each internal passage of interest of a device mounted in said cassette in one direction and external pressurization above the pressure in said cassette will induce a desired amount of net transient flow in each of said internal passages of interest in the opposite direction wherein the amount of net transient flow in each of said internal passages of interest in each direction is greater than the volume of each passage of interest.

23. The container of claim 21 further comprising gas permeable material at said partition openings to expose the portion of each device of interest extending therethrough within each of said openings to the ambient atmosphere.

24. The container of claim 21 wherein said partition openings are designed for clearance with respect to each device of interest passing therethrough.

25. The container of claim 21 wherein the cassette is provided with a gas permeable vapor transport area open to the exterior in both of said compartments.

26. The container of claim 25 wherein said vapor transport areas in said two compartments have unequal vapor transport capacities for allowing the passage of vapor between said cassette and external ambient.

27. The container of claim 25 wherein said compartments are of unequal volume and gas permeable access areas in said two compartments are substantially equal in transport ability.

28. The container of claim 21 wherein said two compartments of said cassette are unequal in volume.

29. The container of claim 28 wherein the cassette is provided with a gas permeable access area open to the exterior in both of said compartments.

30. The container of claim 27 wherein said two compartments of said cassette are unequal in volume.

31. The container of claim 21 wherein the two compartments are of unequal size and gas permeable access areas open to external ambient are located in both compartments.

32. The container of claim 31 wherein the volumes of said two compartments are sufficiently large and different such that net transient flow induced through each passage of interest during a normal pressure cyclic pressure change is greater than the volume of each passage of interest.

33. A gas sterilization system for the sterilization of devices having one or more discreet, elongate, internal passages of interest comprising:
(a) a sterilization container comprising:
(1) a first sterilization chamber enclosing a first volume;
(2) a second sterilization chamber enclosing a second volume in said first sterilization chamber, said second sterilization chamber being smaller than said first chamber wherein said second sterilization chamber is a removable closed chamber connected to one end of said passages of interest wherein said removable closed chamber has a volume greater than the total volume of said passages;
(3) partition barrier to separate said first and second sterilization chambers, said barrier means further being provided with one or more device passage openings therein to accommodate passage of a portion of a device to be sterilized therethrough such that each internal passage of interest to be sterilized in said device has a passage opening exposed to each of said chambers;
(4) means selected from the group consisting of a layer of gas permeable material and a gas permeable opening in each of said one or more device passage openings to permit sterilant vapor to reach and sterilize that portion of a device situated in a barrier opening;

(b) evacuation system disposed to draw a vacuum in both of said chambers reducing the pressure in said chambers at an unequal rate;
(c) pressurized sterilant gas introducing system disposed to introduce sterilant gas into both of said chambers to repressurize said chambers at an unequal rate; and
(d) control system for sequentially operating said evacuation system and said sterilant gas introducing system in a manner to induce a reversing transient net flow between the chambers in each internal passage of interest.

34. The gas sterilization system of claim 33 wherein said second sterilization chamber is a removable closed chamber connected to one end of said passages of interest wherein said removable closed chamber has a volume greater than the total volume of said passages.

35. The gas sterilization system of claim 33, further comprising a sterilization vessel for containing one or more of said sterilization containers, said sterilization vessel being connected to said evacuation system and said sterilant gas phase introducing system.

* * * * *